United States Patent [19]
Bobrick et al.

[11] 4,032,775
[45] June 28, 1977

[54] ILLUMINATION SYSTEM

[75] Inventors: Mitchell Bobrick, Redondo Beach, Calif.; Murray L. Quin, St. Louis; Morris M. Buzan, St. Charles, both of Mo.

[73] Assignee: Emerson Electric Co., St. Louis, Mo.; a part interest

[22] Filed: Oct. 24, 1975

[21] Appl. No.: 625,586

Related U.S. Application Data

[62] Division of Ser. No. 496,879, Aug. 12, 1974, Pat. No. 3,936,671.

[52] U.S. Cl. .............................. 240/73 R; 240/78 R; 248/326
[51] Int. Cl.² .................................. F21S 1/00
[58] Field of Search ............... 240/52 R, 73 R, 67, 240/70, 78 R; 248/324, 326, 336, 337

[56] References Cited

UNITED STATES PATENTS

| | | | |
|---|---|---|---|
| 1,761,832 | 6/1930 | Johansson | 248/326 |
| 2,115,898 | 5/1938 | Zogora | 240/70 X |
| 2,659,827 | 11/1953 | Scag et al. | 248/326 X |
| 2,802,094 | 8/1957 | Grosz | 240/52 R X |
| 2,809,281 | 10/1957 | Greppin | 240/52 R X |
| 3,354,301 | 11/1967 | Bobrick | 240/73 R X |
| 3,426,190 | 2/1969 | Bobrick | 240/73 R |
| 3,718,816 | 2/1973 | Seelbach et al. | 240/52 R |
| 3,736,417 | 5/1973 | Williams | 240/78 R |

Primary Examiner—R. L. Moses
Attorney, Agent, or Firm—Polster and Polster

[57] ABSTRACT

An illumination system, particularly adapted to use in hospitals, has an elongated, low-profile fluorescent lighting fixture on the side of and parallel to a track, a reading-examination light mounted on one end of a telescoping boom, the other end of which is swingably connected to a boom mount rotatably carried by a carriage mounted to roll along the track. The lighting fixture includes means for providing low brightness down lighting and higher brightness side lighting. The reading-examination light is so constructed as to permit two levels of illumination from a single light source and color correction in a small, balanced, easily manipulated unit. The telescoping boom and its mounting are so constructed as to be light, strong and stable in any position within wide limits. The carriage is so constructed as to permit easy transport of the boom and light, and positive and continuous connection of electrical conductors within the boom to a source of current.

11 Claims, 26 Drawing Figures

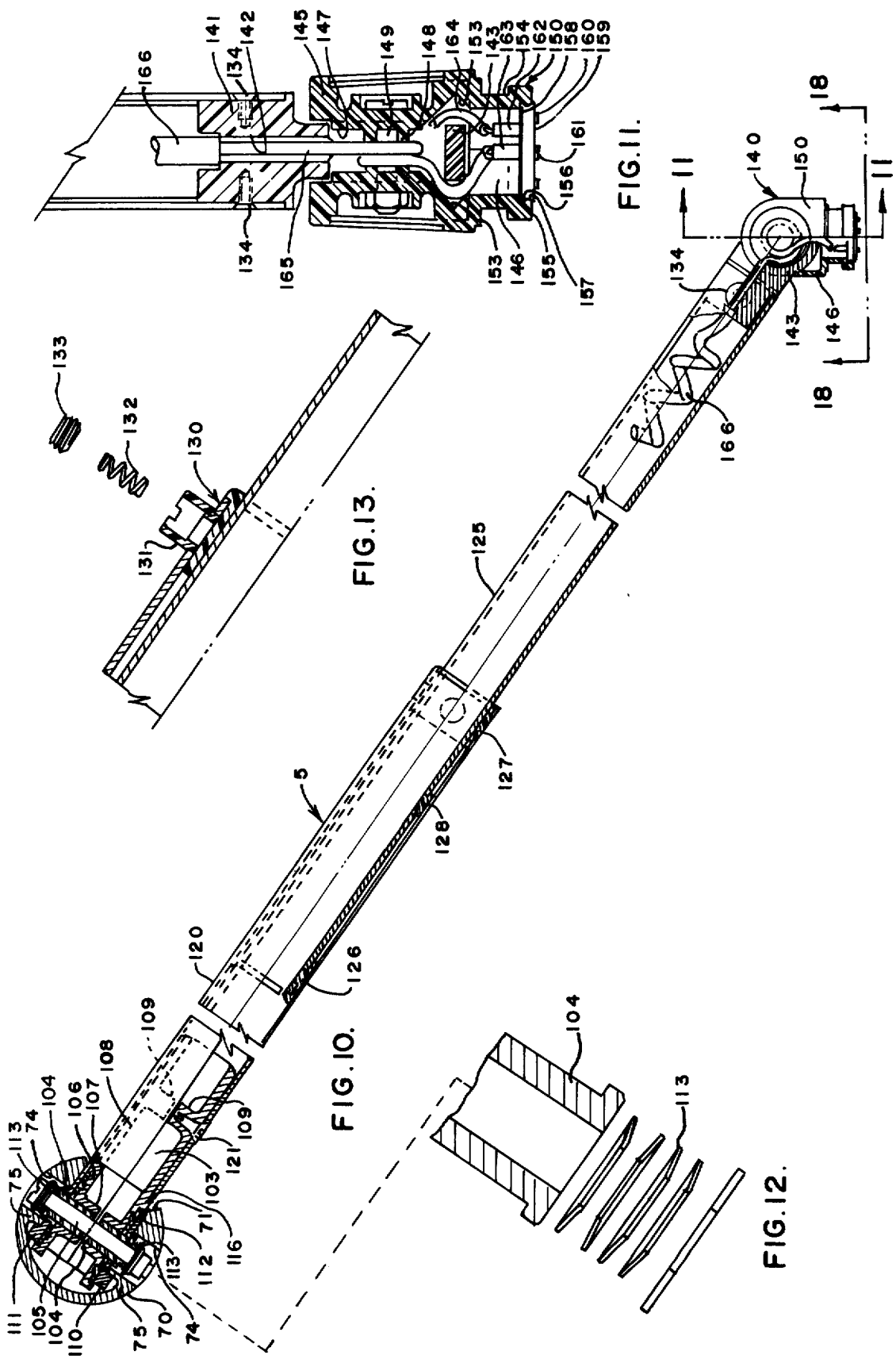

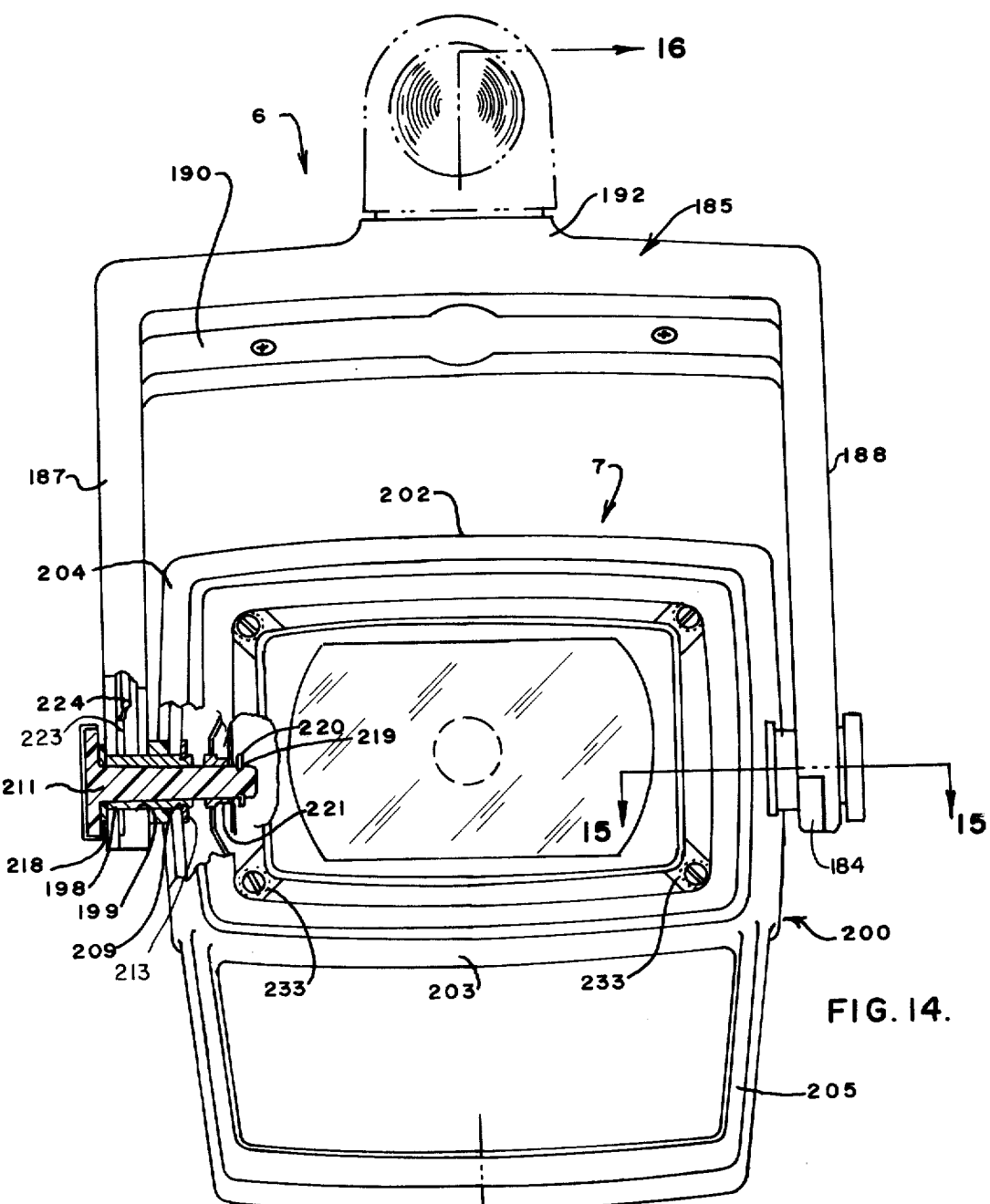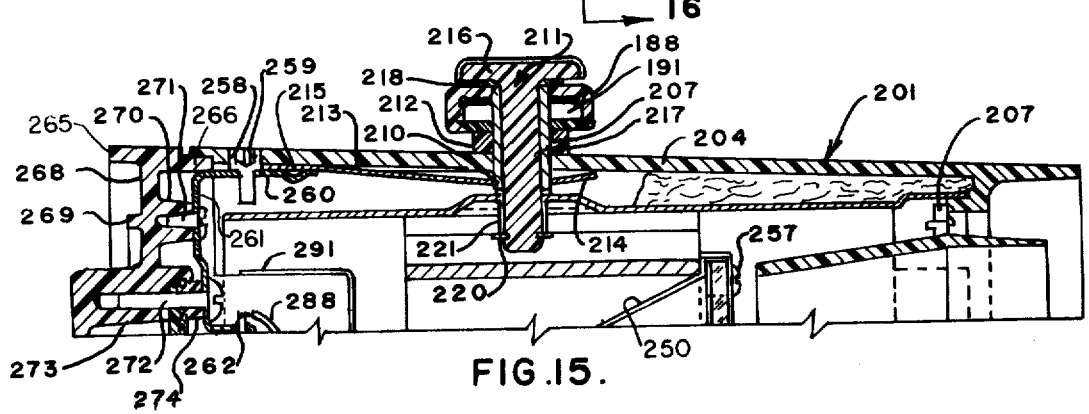

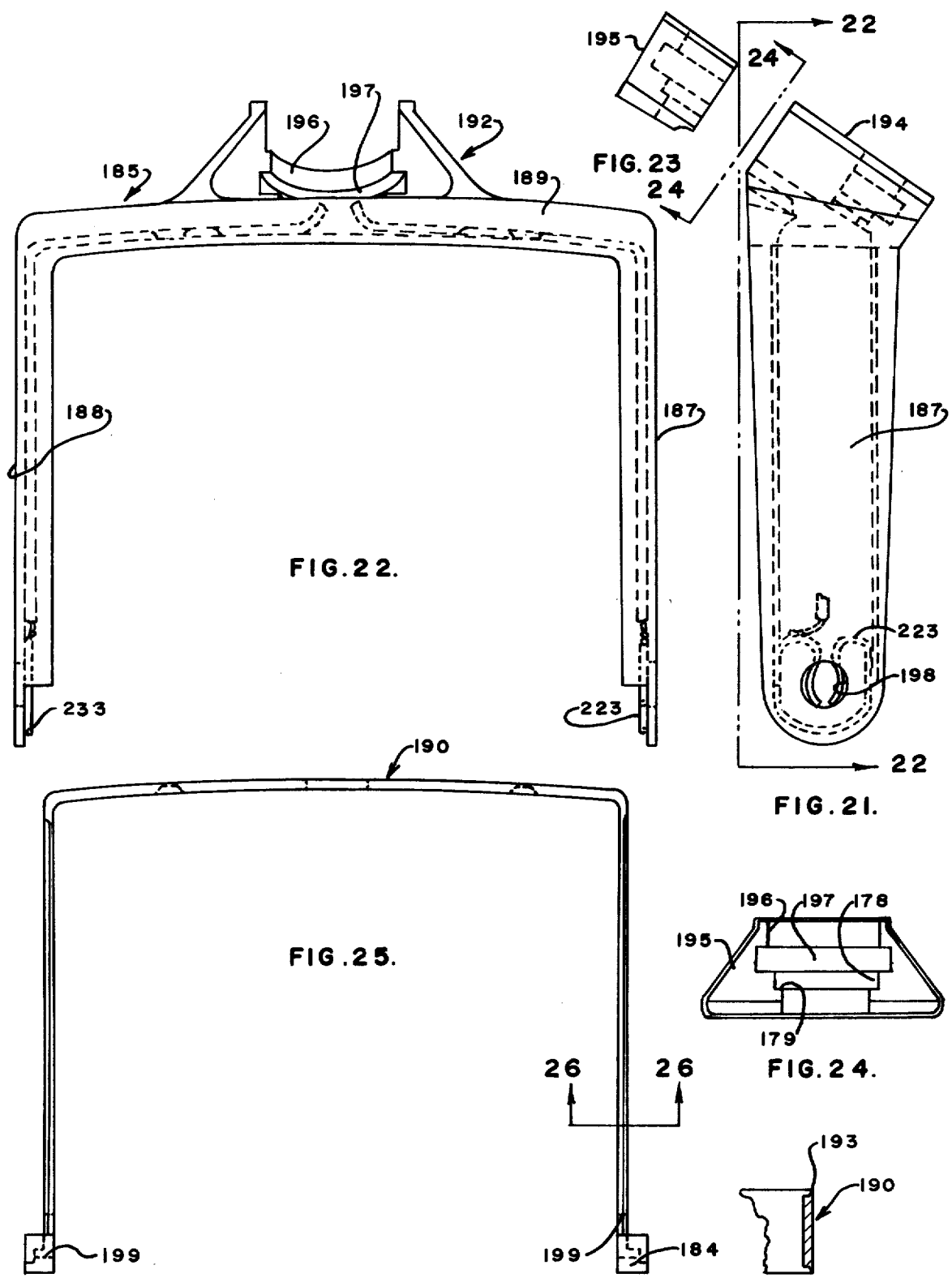

ILLUMINATION SYSTEM

This is a division of application Ser. No. 496,879 filed Aug. 12, 1974 now U.S. Pat. No. 3,936,671.

BACKGROUND OF THE INVENTION

In the horizontal run-through utility and service system illustrated and described in Bobrick U.S. Pat. No. 3,354,301, elongated lighting fixtures are shown as positioned on either side of a central curtain track, to provide illumination on either side of a central curtain to permit the division of a room into two private areas with identical overhead lighting. No provision is suggested in the Bobrick arrangement for a travelling reading and examination light.

One of the objects of this invention is to provide, in a horizontal run-through type system, low-profile lighting fixtures with improved means for providing low brightness down lighting and higher brightness side lighting.

Another object is to provide, in a horizontal run-through system, either one or a pair of lengthwise travelling reading-examination light-carrying booms mounted at their upper ends for rotation and adapted to be self-supporting within a wide arc.

Still another object is to provide such a system in which an improved reading-examination lamp is mounted on the outer end of the telescoping boom, and so constructed as to permit two levels of illumination from a single light source.

Other objects will become apparent to those skilled in the art in the light of the following description and accompanying drawings.

BRIEF SUMMARY OF THE INVENTION

In accordance with this invention, generally stated, in an illumination system, particularly adapted to use in hospital rooms wherein a central curtain track is flanked by lighting boom-carrying tracks, and two, spaced, elongated fluorescent lighting fixtures are positioned one on either side of the carriage tracks, an elongated enclosure is provided with an open-topped primary enclosure having translucent high brightness light transmitting side and bottom walls and an L-shaped diffusing insert, mounted within the primary enclosure, having low brightness light-transmitting side and bottom walls, the side wall of the diffusing insert extending along the side wall of the primary enclosure next to the lighting boom carriage track. A four-wheeled, elongated carriage is mounted in at least one of the carriage tracks, the carriage carrying a telescoping boom swingably mounted at one end on a boom mount carried by the carriage. The boom mount is mounted for limited rotation and clutch means are provided for holding the boom mount and boom in any desired position within the limits of rotation of the boom.

A yoke, mounted on the outer end of the boom in such a manner as to be self-leveling carries a light head or reading-examination light. The yoke is mounted for rotation and the light head is mounted for rotation within the yoke. Means are provided for making electrical connection between the yoke and light head. The light head is provided with a deeply recessed color-correcting filter, an effective heat sink structure, and an arrangement whereby the power supply to a lamp is automatically disconnected when the light head is disassembled for relamping.

Electrical power supplied to the lamp in the light head by means of a flexible conductor enclosed within the boom, which is electrically connected to a flat tape conductor one end of which is carried by the boom carriage and the other end of which is fixed, the flat tape conductor being so arranged as to provide a positive electrical connection through the full longitudinal travel of the carriage on its track.

DESCRIPTION OF THE DRAWINGS

In the drawings,

FIG. 10 is a view in side elevation, partly in longitudinal section and partly broken away of the boom shown in FIGS. 1 and 2;

FIG. 11 is a sectional view taken along the line 11—11 of FIG. 10;

FIG. 12 is an enlarged fragmentary view, partly in section, of a part of the mounting assembly of the end of the boom adjacent the carriage;

FIG. 13 is an enlarged fragmentary detailed view, partly in section, of a slip joint of the telescoping boom;

FIG. 14 is a view in end elevation, partly broken away, of the yoke and reading-examination light assembly at the outer end of the boom;

FIG. 15 is a fragmentary sectional view taken along the line 15—15 of FIG. 14;

FIG. 21 is a view in side elevation of part of the yoke assembly;

FIG. 22 is a view in rear elevation in the direction indicated by the line 22—22 of FIG. 21;

FIG. 23 is a view in side elevation of a yoke swivel boss insert;

FIG. 24 is a view in front elevation in the direction indicated by the line 24—24 of FIG. 23;

FIG. 25 is a view in rear elevation of a closure for the yoke assembly; and

FIG. 26 is a sectional view taken along the line 26—26 of FIG. 25.

DESCRIPTION OF THE PREFERRED EMBODIMENT

Figure 1:
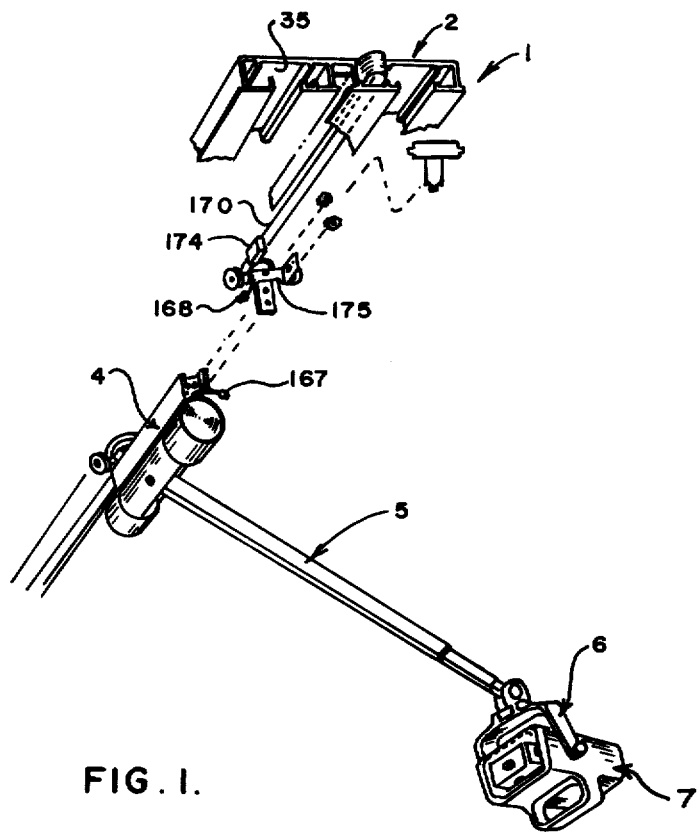
FIG. 1 is a fragmentary view in perspective of one embodiment of system of this invention with the fluorescent lighting fixtures removed to show portions of a carriage assembly in exploded condition.
Figure 3:
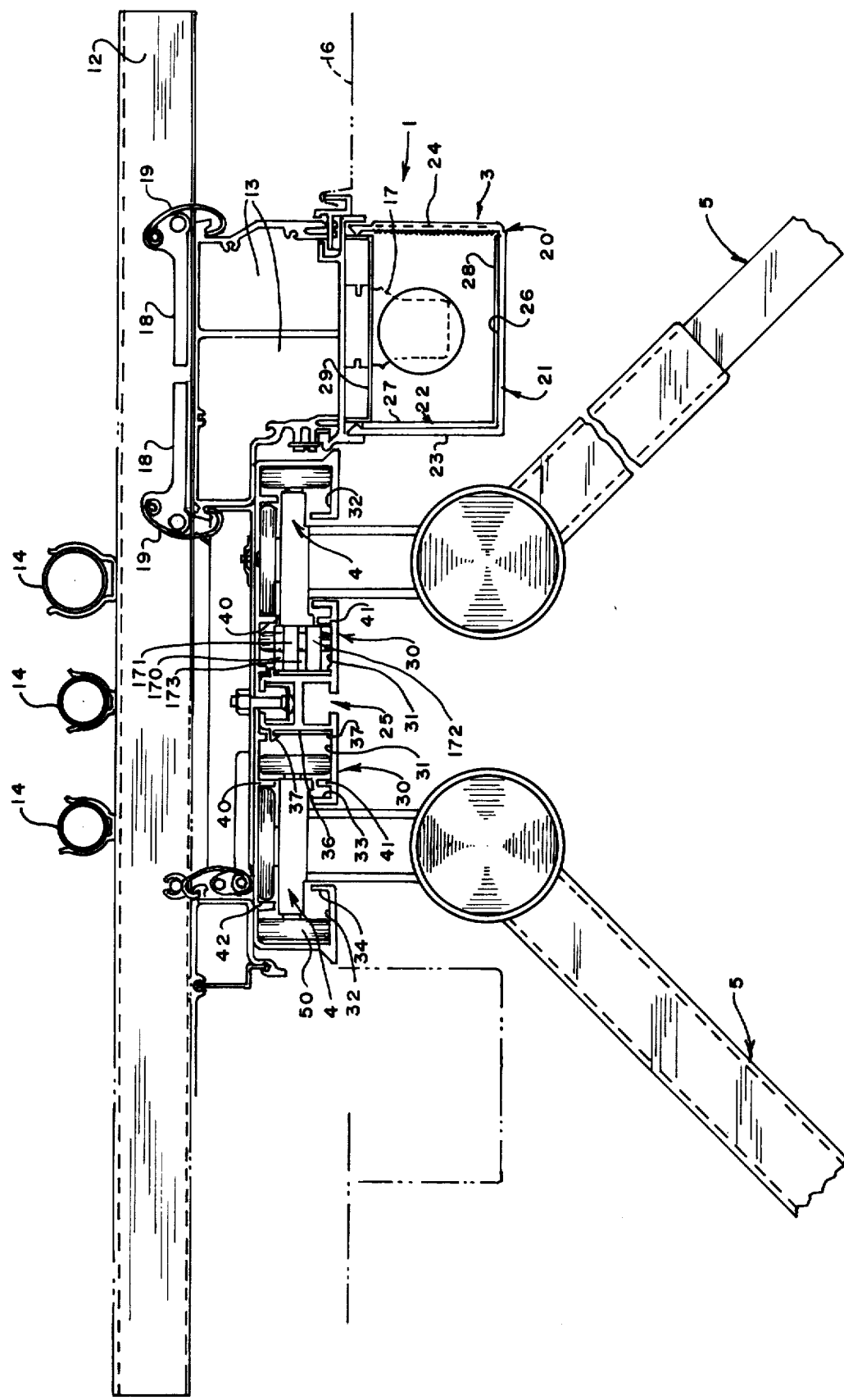
FIG. 3 is a transverse sectional view showing a carriage track and curtain track arrangement, and one of two fluorescent enclosures.

Referring now to the drawings, and particularly to FIGS. 1 and 3, reference numeral 1 indicates an illumination system of this invention which includes a track and mounting system 2, fluorescent lighting fixtures 3, boom-carrying carriages 4, telescoping booms 5, self-leveling yoke assemblies 6 and reading-examination lights 7. The system illustrated is described as applied to hospital rooms, in which a horizontal run-through core is provided and vertical take-off consoles extend down the wall of each room at the head of beds, sometimes referred to as the reference wall.

The track and mounting system 2 is supported by rails 12, extending transversely of the length of the track and mounting system. In the embodiment shown, the track and mounting system consists of long aluminum extrusions formed to provide wireways 13 which not only serve as housings for electrical conductors for hospital electrical wiring, nurse calls, telephone lines and the like but also serve as means for mounting ceiling panels 16 shown in phantom lines in FIG. 3, sockets 17 for fluorescent lamps, and enclosures 20 for the fluorescent lighting fixtures 3. Medical gas pipelines 14 are mounted on the rails 12, above and parallel to the wireways, as shown in FIG. 3. In this embodiment, the track and mounting system is clamped to the rails by means of levers 18, pivotally mounted on a vertical web of rails 12, and hooks 19, arranged to overcenter with respect to the pivot arm of the levers and to engage channels on the wireways. The tracks are mounted to the wireways in a similar way as shown in FIG. 3. The track and mounting system includes a central curtain track 25, with spaced, oppositely directed feet defining a slot of conventional construction. Flanking the curtain track 25 on either side, is a carriage track 30. Each of the carriage tracks 30 has an inner ledge 31 and an outer ledge 32. The inner ledge 31 has at its outboard edge an upstanding rim 33, which, with an upstanding rim 34 along the free edge of the outer ledge 32 defines a carriage channel 35. Extending along an inner wall 36 at the inner edge of the inner ledge 31 are conductor tabs 37. Vertically aligned but spaced guide rails 40 and 41 are positioned inboard of the rim 33 of the inner ledges 31. An outer guide rail 42, positioned symmetrically with respect to the center line of the carriage channel 35, depends from a top wall above the outer ledge 32.

As seen in FIG. 3, the lighting fixtures 3 are positioned outboard of and on either side of the outer ledges 32. The enclosures 20 are made up of two parts, a primary enclosure 21 and an L-shaped diffusing insert 22. The primary enclosure 21 is preferably made of clear plastic such as acrylic, and has an inside side wall 23, an outside side wall 24 and a bottom 26 with smooth, planar inner and outer broad surfaces. In the embodiment shown, the side wall 24 is indicated as being provided with transverse prisms on the outside and longitudinal prisms on the inside. The diffuser 22 has a side wall 27 and a bottom wall 28, both of a translucent, light-diffusing plastic such as pigmented acrylic with a transmission of approximately ten percent. It has been found that the best light control, for providing low brightness down lighting and lighting through the inside side wall is obtained by merely mounting the diffuser 22 loosely within the primary enclosure 21, as indicated in FIG. 3. As shown in that figure, the upper edge of the diffuser side wall 27 may be trapped between the inside side wall of the enclosure and a wireway cover 29.

It will be understood that, depending upon the length of fluorescent tubes, the primary enclosure and diffuser will be in convenient lengths, and can be supported at their ends on straps, preferably inverted T-shaped in cross section, carried by the mounting system.

Figure 6:
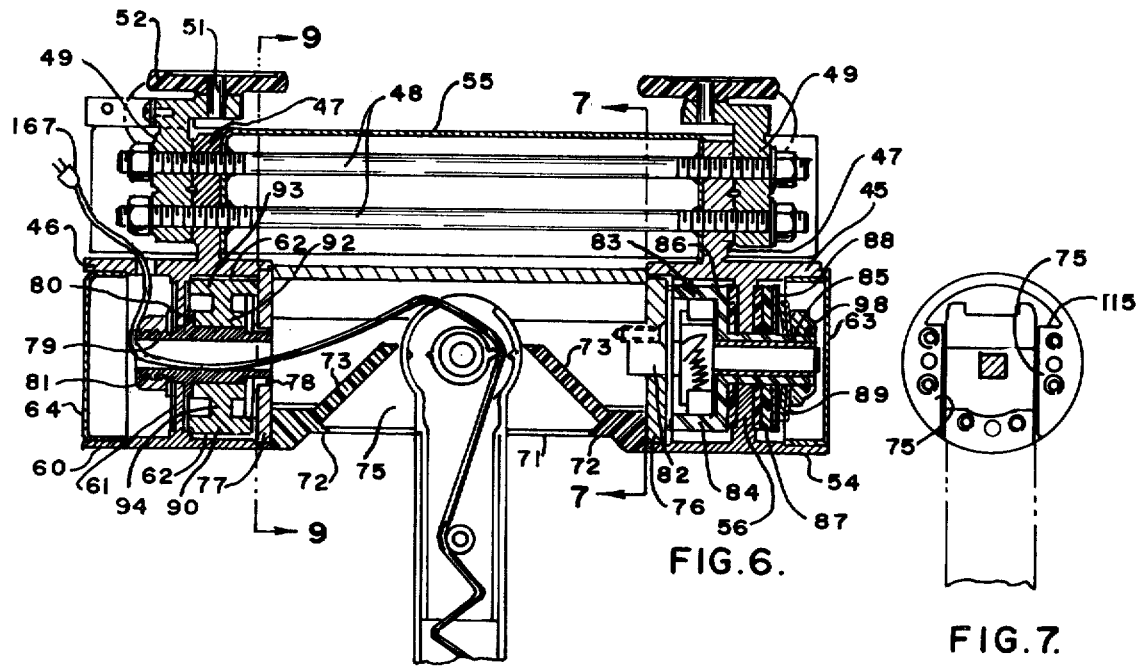
FIG. 6 is a sectional view taken along the line 6—6 of FIG. 5.

Referring now particularly to FIGS. 1 and 3 through 9, the carriages 4 in this embodiment include a near or clutch end casting 45 and a far or retard end casting 46. The terms "near" and "far" are used to signify the positions of the ends with respect to the reference wall, both carriages being mounted in tracks with the clutch end nearer the reference wall. The clutch and retard end casting 45 and 46 have upstanding end blocks 47, with vertically spaced and lengthwise aligned holes in them, to receive throughbolts 48. The throughbolts 48, with nuts on their threaded ends, serve to fasten wheel blocks 49 to the outboard faces of the end blocks 47. The wheel blocks 49 carry four carriage supporting wheels 50, which are journaled on axles projecting from opposite sides of the wheel blocks 49, as shown in FIG. 6. The wheel blocks 49 also carry vertical axles 51, upon which guide wheels 52 are revolvably mounted.

The end blocks 47, hence the clutch and retard end castings, are spaced by a spacer body 55, against the ends of which the inboard faces of the end plates 47 are drawn by the throughbolts 48.

The clutch end casting 45 includes a cylindrical end bell 54 with a heavy annular inner wall 56 extending radially inwardly intermediate the ends of the end bell 54. The inside surface of the end bell 54 at both axial ends is rabbeted.

The retard end casting 46 includes a cylindrical end bell 60, which has a radially inwardly extending annular wall 61, and axial splines 62. The inner wall at both ends of the retard end casting end bell is also rabbeted at both axial ends of the cylindrical end bell. Cover caps 63 and 64 are friction mounted in the rabbeted outer ends of the end bells 54 and 60 respectively.

Figure 7:
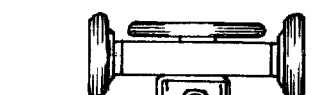
FIG. 7 is a sectional view taken along the line 7—7 of FIG. 6.

Carried by and between the facing ends of the end bells 54 and 60 is a boom sleeve or mount 70. In the embodiment shown, the boom mount 70 is a heavy aluminum extrusion. The boom mount 70 is generally cylindrical on its outside, with a rectangular slot 71 extending through its full length. The rectangular slot 71 is bounded along its long sides by heavy chordal sections 75 chamfered at their outer edges and terminating in a ledge 115 on their inside edges, all as best shown in FIG. 7. In the assembled mount, the slot 71 is bounded at its axial ends by heavy sectioned boom stops 72, with which inwardly convergent but spaced cross walls 73 are integral. The stops 72 and cross walls 73 are, in this embodiment, plastic inserts.

Figure 8:
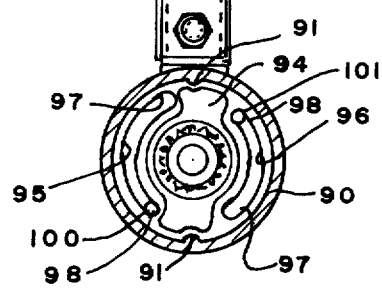
FIG. 8 is a view partly in end elevation and partly in section taken along the line 8—8 of FIG. 4, the opposite end from that shown in FIG. 5.
Figure 9:
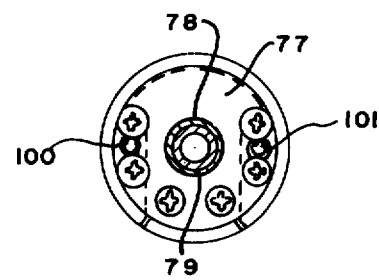
FIG. 9 is a sectional view taken along the line 9—9 of FIG. 6.

The cylindrical boom mount 70 is closed at its ends by boom mount end plates 76 and 77, which in this embodiment are made of steel, mounted on the ends of the boom mount by means of screws extending into tapped holes in the end faces of the heavy chordal sections 75, as indicated in FIG. 9. The plastic inserts which include the stops 72 are fastened by screws to the end plate, as indicated in FIGS. 7 and 9. The end plates 76 and 77 are round in front elevation, as indicated in FIG. 9, and fit rotatably within the channels formed by the rabbeting of the facing ends of the end bells 54 and 60. The end plate 77 has a central opening in which a bushing 78 is mounted, and the bushing in turn is revolvably mounted on the inner end of a hollow stop end shaft 79. The shaft 79 has a stepped inner end on which the bushing 78 is journalled, an annular collar 80 integral with the shaft, and an externally threaded outer end 81. The shaft 79 is mounted in the end bell 60 by means of a nut screwed onto the threaded end 81 against a lock washer which bears against the outer face of the annular wall 61, while the collar 80 bears against the inner face of the wall 61, clamping the shaft firmly in place. A retard-stop disc 90 is mounted on the shaft 79, in close engagement with the inside wall of the end bell 60 between the end plate 77 and the annular wall 61. The retard-stop disc 90 has a pair of grooves 91, as illustrated in FIG. 8, into which the splines 62 extend, to fix the disc 90 against rotation relative to the end bell. The disc 90 has a hub 92, a rim 93 which is axially wider than the hub 92, a web 94 between the hub and the rim, and heavy arcuate spaced ribs 95 and 96. The ribs 95 and 96 define oppositely disposed arcuate passages extending axially entirely through the disc 90. The passages are not uniformly wide radially, being, in the embodiment shown, wider by approximately one thousandths of an inch through about 55° of arc from an end 97 than through approximately 35° of arc from the other end 98. The meeting edges of the two sections are relieved to provide a short inclined transition area.

Rollpins 100 and 101 are fixed in and extend axially from the end plate 77 diametrically opposite one another as shown in FIG. 8. The rollpins 100 and 101 fit snugly in the wider part of the passages defined by the ribs 95 and 96, respectively, but tightly in the narrower part.

The end plate 76 has a square hole in its center, through which a square shaft 82 of a one-way roller clutch 83 extends. The roller clutch 83 is of conventional construction, with spring biased rollers mounted to roll along inclined planes on the periphery of a plate secured to the shaft 82, and engaging the inner surface of a cup 84 secured to a hollow shaft 85 threaded at its outer end to receive a nut.

The retard-stop disc 90 and the one-way roller clutch 83 must be oriented and constructed respectively for use with right and left hand carriages. The rest of the carriage and boom mounting assembly elements are symmetrical with respect to a vertical center plane.

In this embodiment, a clutch disc 86 is mounted on the shaft 85 between the bottom of the cup 84 and the annular inner wall 56, and clutch disc 87 is mounted on the shaft between the opposite radial face of the clutch ring 56 and a clutch plate 88. The clutch plate 88 has a non-circular opening complementary to flats on opposite sides of the shaft 85 extending between the outer end of the shaft 85 and the inner wall 56. The clutch plate 88 is biased against the clutch disc 87, and the radial surface of the cup 84 is biased against the clutch disc 86, which in turn is biased against the inner wall 56 by Belleville washers 89, against which a stopnut 98 is screwed down to the desired degree of tightness.

Referring now to FIGS. 6 through 11, as shown in FIG. 10, passages 74 aligned at right angles to the radial center plane of the slot 71 extend transversely through the heavy chordal sections 75 of the mount 70. The boom 5 is mounted in the boom mount 70 by means of a pintle 105, the ends of which are within the passages 74. A boom mount end fitting 106 is made in two parts, as indicated in FIG. 10. Each of the parts of the boom fitting has a skirt 103 extending all the way around it except for its lengthwise outer ends which are open, the edges of the skirts abutting when the two parts are assembled. The two parts are mirror images, and each has an integral sleeve 107, and a stem 108, with a screw boss 109. Bushings 104, mounted in the sleeve 107 and on the pintle 105, have an annular flange at their outer ends, which engage the periphery of holes in brake discs 110. The brake discs 110 are circular in front elevation, but have a chordal boss 111 at one end, which engages the ledge 115 of the section 75 on either side of the boom mount 70. The fitting 106 has a circular face bounded by a rim 116, in which a clutch washer 112 is seated. The clutch washers 112 have projections on one side which extend into shallow indentations in the circular faces of the fitting. The other face of the clutch discs engages a flat face of the brake discs 110. The pintle 105 has a head at one end, between which and the outer end of one of bushings 104 is a group of spring washers 113. Similarly, the pintle has a nut on the other end, between which and the other end of the bushings 109 is a group of spring washers 113. The bushings, spring washers, head and nut are all of a lesser diameter than the passages 74 in the boom mount. Tightening of the nut on the pintle will provide whatever degree of bias is required to give the desired amount of clamping of the clutch discs 112 between the brake discs 110 and the circular faces of the fitting.

A square seamless hollow upper boom tube section 120 is mounted on the stem 108 of the fitting 106 by means of screws 121 screwed into the screw bosses 109 of the fitting. In the embodiment shown, the boom 5 is made in two telescoping sections. A lower tubular section 125 is dimensioned to slide within the section 120. A plastic sleeve bushing 126 with a lip at its outer end and a projection on its inner side which takes into a hole in the lower tubular section 125 near its upper end and a sleeve bushing 127 with a lip on its outer end and a projection taking into a hole in the upper section 120 near its lower end, serve to make the movement of the inner section 125 and the outer section 120 quiet, and to insulate the two metal tubular sections electrically from one another. A button 128 with a stem projecting into a hole in the wall of the inner section 125 serves as a stop. An arm glide brake 130 in this embodiment consists of an externally and internally threaded nipple 131 screwed into an internally threaded hole near the lower end of the upper section 120 immediately contiguously the outer surface of the sleeve bushing 127. A helical compression spring 132 bears at one end on the outer surface of the sleeve bushing 127, and at the other end on the inner face of a threaded plug 133, as shown in detail in FIG. 13.

At its lower end, the boom 5 carries a yoke fitting 140. The yoke fitting 140 has a square block 141 with a passage 142 through it, and terminates at its lower end in a parallel flat sided ring 143, the block 141 is mounted in the lower end of the boom section 125 by means of screws 134 extending through holes in the side walls of the section 125 and into the block. A yoke hinge 145, made in two mirror image parts, forms a wire housing, hinge knuckle and swivel bearing. Each of the parts of the yoke hinge 145 has a skirt 146, shown in FIGS. 10 and 11, edges of which abut when the yoke hinge is assembled, as shown in FIG. 11. The skirt terminates just short of the ring 143, as shown in FIG. 10. The yoke hinge also includes rotating-bearing circles 147, which project within the compass of the ring 143 as shown in FIG. 11 revolvably to mount the yoke hinge on the ring part of the yoke fitting 140. Pintle bosses 148, concentric with the rotating-bearing circles 147 project inboard from the circles 147, and are provided with a passage extending entirely through the bosses and circles to receive a pintle 149. The pintle 149 has a slotted head at one end and a nut at the other.

Clearance notches 153 interrupt the rotating-bearing circles at two points. The yoke hinge 145 includes a yoke swivel bearing section 150, with a neck 154 and a swivel collar 155 defining a channel. At the lower end of the yoke swivel bearing section, which is circular in bottom plan, the inner surface of the swivel collar is rabbeted to provide a seat 156. Two diametrically disposed fingers 157 are spaced from the bottom of the seat, and project radially inwardly. The fingers 157 serve a double purpose, that of retaining a spring washer 158 in the bottom of the seat, and of locating an insulating disc 159, which is provided with notches in its perimeter to receive the two fingers. The insulating disc 159 carries on its outer face an outer contact ring 160 and a center contact plate, concentric with but spaced from the outer contact ring. The outer contact ring is electrically connected to an outer contact ring lead 162. The center contact plate 161 is electrically connected to a center contact plate lead 163. The two leads 162 and 163 project into the housing defined by the yoke hinge, and are electrically connected to electrical conductors 164 and 165 respectively. The conductors 164 and 165 are wrapped in opposite directions around the pintle bosses 148, which, being part of the yoke hinge, are made of electrically insulative plastic, as is the yoke fitting 140. The conductors 164 and 165 then enter and become part of a helically formed retractile cord 166, shown in FIGS. 6 and 10, wound in such a way as to provide ample allowance for the extension and retraction of the boom sections 120 and 125 with respect to one another. The other end of the cord 166 is brought out through the open inner end of the boom fitting 106, as shown particularly in FIG. 6, through the hollow shaft 79, through a hole in the end bell of the brake end casting 46, to a quick-connect plug 167 to which the conductors 164 and 165 are electrically connected.

Figure 4:
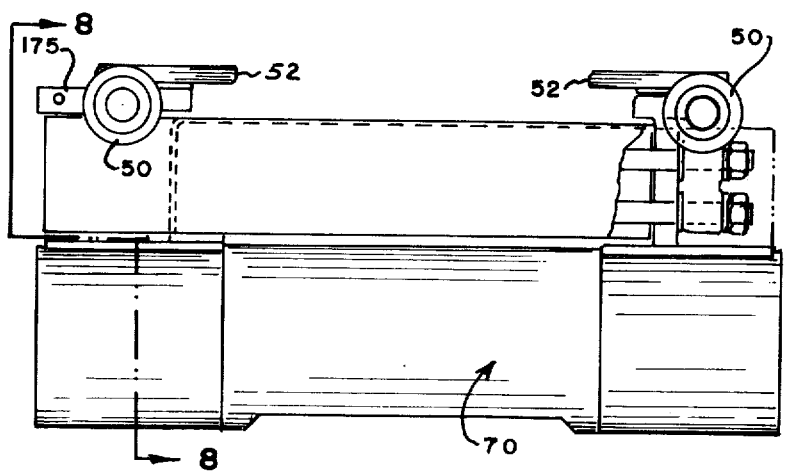
FIG. 4 is a view in side elevation of one carriage, partly broken away.
Figure 5:
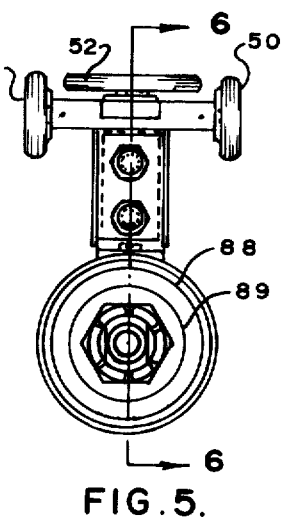
FIG. 5 is a view in end elevation of the carriage shown in FIG. 4.

A complementary plug fitting 168 is connected to conducting strips 171 and 172 of a flat tape conductor 170, best shown in FIGS. 1 and 3. The conducting strips 171 and 172 are spaced apart and lie beneath broad surfaces of an insulative strip 173, to form the tape conductor 170. One end of the flat tape conductor 170 is mounted in an insulation block 174, from which the plug 168 extends. The insulation block 174 is mounted on a bracket 175 carried by the wheel block on the outer, retard end casting 46, as shown in FIGS. 1, 4 and 6.

The other end of the flat tape conductor 170 is electrically connected to conductors at the wall end of the track and mount system contiguous the head ends of hospital beds as illustrated in FIG. 1 of Bobrick U.S. Pat. No. 3,354,301. Between its ends, the flat tape conductor is looped, as indicated in FIG. 1, the looped conductor being housed in a channel defined in part by the inner ledge 31 of each of the carriage tracks, as shown in FIG. 3. Through a short distance less than half of the total reach of the flat tape conductor 170, the conductor is held flat against an inner wall 36 by the conductor tabs 37. It will be noted that the conducting strips 171 and 172 are spaced inwardly from the top and bottom edges of the insulative strip, as shown in FIG. 3, so that the strip can be notched to traverse conductor tabs 37 at the desired distance.

The flat tape conductor 170 is completely flexible in the dimension shown in FIG. 1, so that the conductor can be flexed in the movement of the carriages 4 indefinitely. It is, of course, necessary that there be sufficient free space in the length of the chamber within which the flat tape conductor runs, to accommodate the tape as it "unrolls" as the carriage is moved away from the fixed, wall end of the tape.

Figure 16:
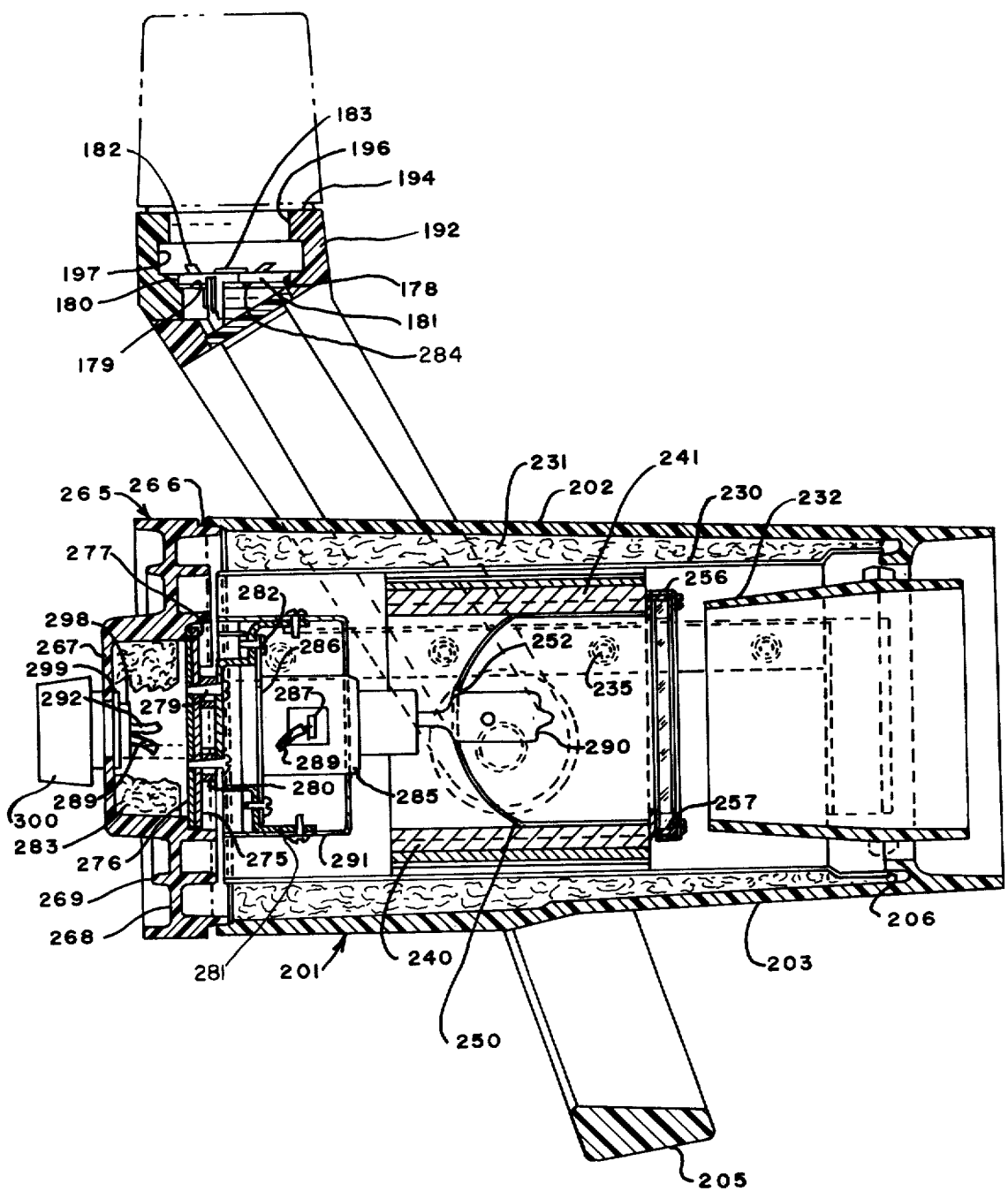
FIG. 16 is a sectional view taken along the line 16—16 of FIG. 14.
Figure 17:
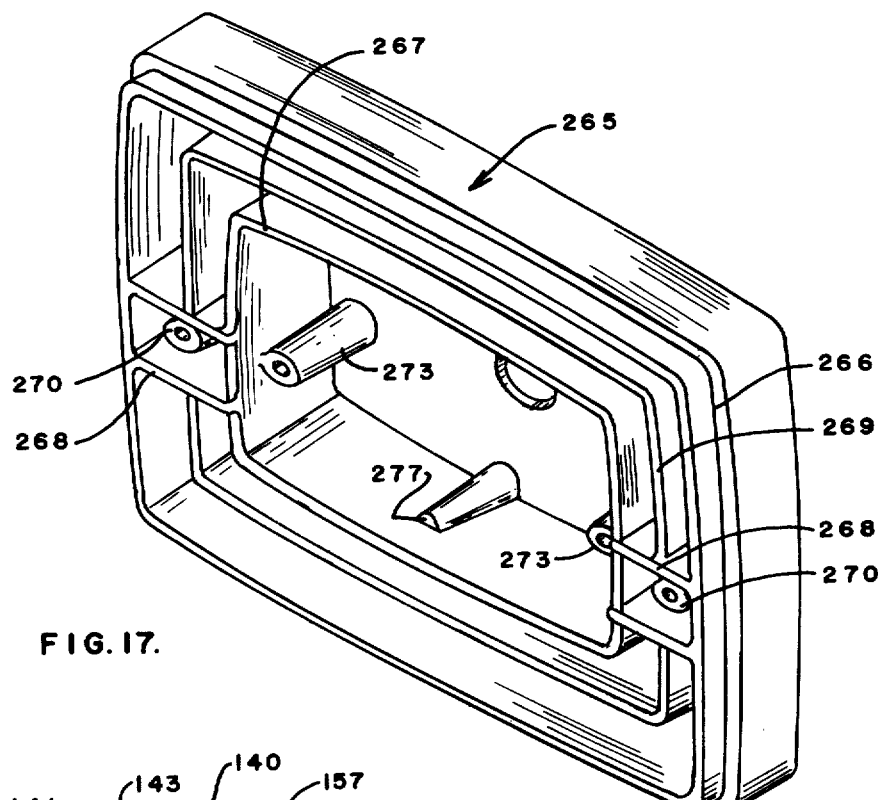
FIG. 17 is a view in perspective of the inner side of the light head housing closure of the reading-examination light assembly.
Figure 18:
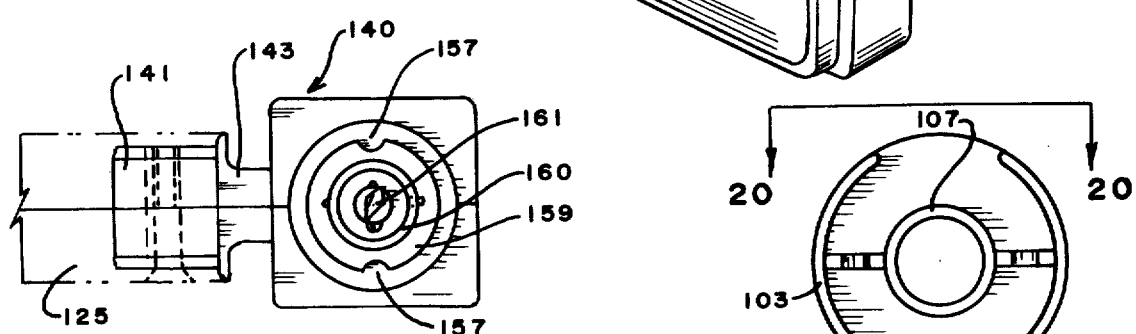
FIG. 18 is a bottom plan view of a yoke fitting at the lower end of the boom.
Figure 20:
FIG. 20 is a top plan view in the direction indicated by the line 20—20 of FIG. 19.
Figure 19:
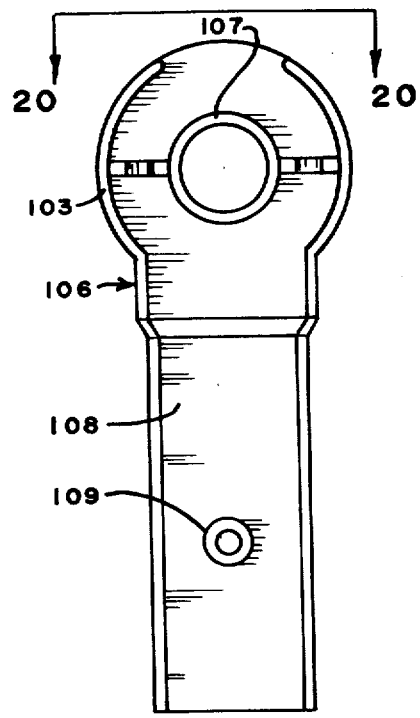
FIG. 19 is a view in side elevation of the inner side of one of two identical parts of a boom fitting at the upper end of the boom.

Referring to FIGS. 10–16, at the outer end of the boom 5, the yoke assembly 6 includes a yoke 185 which serves not only pivotally to support a reading-examination light 7 but to carry conductors and connections for electrically connecting the conducting strips of the flat tape 170, hence a source of power, to a lamp inside the housing of the examination light. To that end, the yoke assembly 6 includes a yoke 185, made of electrically insulative material, with hollow arms 187 and 188 and a hollow cross bar 189, all with an open channel in an inside face, as shown in FIGS. 14, 15 and 16. A closure 190, also of electrically insulative material, removably mounted in the channel, serves totally to enclose an interior chamber 191, which serves as a wireway. In this embodiment, the closure 190 is U-shaped complementarily to the yoke 185. Legs of the closure are chamfered along their long edges, the chamfers 193 seating within complementary grooves in the channel defining edges of the arms 187 and 188, as indicated in FIGS. 15 and 26. A cross member of the closure has parallel edges, and fits directly into the channel in the yoke cross bar, as shown in FIG. 16. The closure is held in place by screws, as shown in FIG. 14. The two legs have at their lower ends semi-circular walls, as indicated in FIG. 14, and journals 184, fitting into a cut away portion of the side walls of the arms 187 and 188, as shown in FIG. 14. The legs of the closure are flexible, which facilitates assembly of the yoke and a light head.

On the outer face of the cross bar 189, and integral with it, is a swivel boss 192, which has a planar top surface 194, the plane of which lies at an angle to the lengthwise center line of the arms 187 and 188, as shown in FIGS. 14 and 16. The swivel boss 192 is formed with a cavity defined by outwardly convergent side walls and a bottom wall, to receive a swivel boss insert 195. The swivel boss insert, which is mounted by screws, permits the mounting of the yoke assembly 6 on the yoke fitting 140, but, in effect, merely completes the swivel boss. The swivel boss and insert together have a yoke bearing flange 196 complementary to the neck 154 of the yoke hinge 145, and a channel 197 shaped complementarily to the yoke swivel collar 155. The surfaces defining the inside faces of the yoke bearing flange 196 and channel 197 are perpendicular to the planar surface 194.

A circular opening through the swivel boss 192 and insert 195 is defined by a seat 178 with a step 179. The seat 178 has locating tabs 180 extending radially inwardly a short distance. A disc 181, of electrically insulative material, carries on its outer surface an outer contact ring 182 and a central contact plate 183, which when the yoke is mounted on the yoke swivel bearing section of the yoke hinge 145 correlate exactly with the contact ring and center contact respectively of the disc 159 in the yoke fitting. A spring washer 184, held in place axially by the stop tabs 180, is mounted between the step 179 and the inner side of the disc 181. The disc 181 has notches to receive the stop tabs 180 slidably.

At the other ends of the yoke arms, the yoke arms have pivot sleeve passages 198 aligned with one another and extending transversely through the outside side wall of the yoke arms. The closure 190 also has a pivot sleeve passage 199 concentric with a part of the journal 184, as shown in FIGS. 14 and 25. An electrically conducting pivot sleeve 209 is journaled for rotation in the passages 198 and 199 of each arm. The pivot sleeve 209 extends through and is fixed in a thickened section of a side wall 204 of a reading-examination light head 200. The light head 200 includes a housing 201, with a top wall 202, a bottom wall 203 and side walls 204. A handle 205 is made integral with the light head housing 201 and projects from the bottom wall 203.

The light head housing also includes a radiation shield lip 206 which extends around the inside wall of the housing substantially inboard of the mouth of the housing, as shown in FIG. 16, and louver mounting pads 207 slightly inboard of the radiation shield lip 206, as shown in FIG. 15.

As can be seen in FIG. 16, the walls 202, 203 and 204 diverge in a direction away from the mouth of the housing, so that a rear open end is of greater area than the mouth. The inner surface of the housing at its rear end is rabbeted.

As has been indicated, the pivot sleeves 209 extend through the side walls of the housing. They project a short distance into the interior of the housing, and are provided near their inner end with an annular groove 210. The sleeves 209 project a longer distance outwardly from the housing, to accommodate a spacer 212 of electrically insulative material between the side wall 204 and the inside surface of the yoke arms 187 and 188, and to extend through the yoke arms. A yoke pin 211 of electrically insulative material has a stem 217 which extends through the pivot sleeve 209 into the interior of the housing 201, and a head 216 on its outside end. Spacer 218 is shown as mounted between the underside of the head 216 and the yoke arm 188.

Near its inner end, the stem 217 has an annular snap-ring groove 219 in which a snap-ring 220 is seated. A Heyco bushing 221 is mounted on the stem 217 between the snap-ring 220 and the pivot sleeve 209, as shown in FIG. 15.

A radiation shield 230, rectangular in end elevation, and made of reflective material, has its inner end positioned between the radiation shield lip 206 and the inner surface of the walls 202, 203 and 204. The inner end of the radiation shield 230 is flared, as shown in FIGS. 15 and 16, and the space between the radiation shield 230 and the inside surface of the housing 201 is filled with thermally insulative material 231, such as glass wool.

A generally rectangular louver 232, with convergently inwardly directed bounding walls is provided with ears 233 corresponding in position to the louver mounting pads 207 on the housing, and the louver 232 is mounted to the pads by means of screws, as shown in FIG. 14. The size and shape of the louver 232 is such as to leave a passage all the way around the louver, between the louver and the housing and the louver and the radiation shield 230, interrupted only by the small pads and ears by which the louver is mounted.

Inboard of the louver, and mounted within the confines of the radiation shield 230, is a heat sink 240. The heat sink 240 is a heavy extruded aluminum sleeve, with heat radiating fins 240 projecting outwardly from the outside surface of the heat sink, extending, in parallel ranks, fore and aft of the lamp housing, and spaced to provide passages between them for the free flow of air. The radiation shield 230 is made in two C-shaped parts, long side edges of which overlap. The corners of the parts are formed on a radius except through a length intermediate their ends slightly greater than the length of the heat sink, where the corners are embossed outwardly to provide a debossed inside seat of each corner to receive corner fins of the heat sink. The radiation shield and the heat sink 240 are mounted tightly together by rivets 235 which project through the overlapping edges of the radiation shield 230. The caging of the fins in the seats locates the heat sink accurately and precludes shifting of the heat sink. The arrangement also limits the contact between the heat sink and the radiation shield to line contact.

The radiation shield 230 has an opening in it, in which the Heyco bushing 221 is seated, as shown in FIG. 15. The stem 217 of the yoke pin 215 thus projects into a space between the radiation sheild 230 and the wall of the heat sink 240, in a space between successive fins.

Mounted within the heat sink 240 is a reflector 250. The reflector 250 is made of semi-specular material, has an outwardly extending lip 251 with holes in it, and has a lamp receiving opening 252 in a curved rear wall.

A filter 255 is mounted in a U-shaped gasket 257 caged between the lip 251 of the reflector 250 overlying an end face of the heat sink 240 and an L-shaped filter frame 256, which has holes in its corners, aligned with the holes in the lip 251, to receive screws 257, extending into suitable openings in the heat sink 240. The corners of the filter 255 are cut off to permit the screws to clear, and the filter and the filter frame close the end of the heat sink 240.

An electrically conductive spring 213 is mounted in physical and electrical contact with the pivot sleeve 209 in the pivot sleeve group 210. A sort end 214 of the spring 213 bears on the inside surface of the wall 204 on one side of the pivot sleeve 209 and a long end 215 of the spring 213 bears on the inside surface of the wall 204 on the other side of the pivot sleeve near the rear opening of the housing 201. The spring 213 is elongated, and relatively wide as compared with the diameter of the conducting pivot sleeve 209, slopes inwardly of the housing in a direction from its ends toward the groove 210, and is biased tightly into engagement with the inner surface of the wall 204.

Near its outer end, the electrically conducting pivot sleeve 209 is in sliding electrical and mechanical engagement with a double hairpin-type spring contact 223 mounted in the end of the arm of the yoke concentrically with the passages 198 and 199. The hairpin contact 233 is electrically connected to one end of a conductor 224, which extends through the wireway defined by the yoke walls, to one of the contact ring or contact plate in the yoke swivel boss, by way of a lead from the ring or plate.

It will be understood that identical pivot sleeves, yoke pins, electrical contacts and conductors are provided on both sides of the yoke, as indicated in FIGS. 14 and 15.

Near the rear end of the housing 201, passages 258 through the side walls 204 are sized to receive the heads of socket head screws 259. The passages 258 are aligned with the center line of the springs 213, which in turn are parallel to the longitudinal center line of the side walls 204, and perpendicular to the plane defined by the outer edge of the rear end of the housing. Socket head screws 259, of plastic, have a threaded shank, which screws into a hole on the longitudinal center line of a lamp spring contact 260. The lamp spring contacts 260, one on either side, are electrically insulated from one another, and form parts of a lamp and switch assembly carried by a light head housing closure 265.

The light head housing closure 265 includes a stepped peripheral wall 266 which fits snugly within the rabbeted inside wall at the rear of the housing 201, an inverted cup-shaped hub 267, generally rectangular in plan, a spider 268 defining a multiplicity of passages, and an intermediate wall 269, which serves a strengthening, decorative and light-baffling function. On diametrically opposite sides, screw receiving bosses 270 at the junctures of legs of the spider 268 and the intermediate wall 269, receive screws 271, extending through holes in a cross piece 261 of the lamp spring contact 260. Screws 272, extending through holes in the cross piece 261 inboard of the screws 271, are threaded into screw receiving bosses 273 integral with the circumferential wall of the hub 267. The inboard end of the lamp spring contact 260 is bent parallel to the contact leg of the contact spring, to form a lead connecting tab 262. It will be seen from FIG. 15 that the contact leg of the contact spring 260 overlies and is in tight mechanical and electrical contact with the spring 213 at its end 215.

The screw 272, on each side of the hub 267 serves also to mount a stepped socket mounting plate bushing 274 of electrically insulative material, a socket mounting plate 275, through which a reduced shank of the bushing extends and a socket mounting plate insulator 276. The socket mounting plate insulator 276 rests against shoulders 277 provided by support bosses also integral with the circumferential wall of the hub, at the inner open end of the cup-shaped hub 267. The socket mounting plate insulator is made of thermally insulative material. The socket mounting plate is made of metal, and has two internally threaded openings to receive screws 279. The screws 279 mount socket mounting plate bushings 280 and a socket bracket 281, to which a socket 285 is fastened by means of a mounting bar 286 and screws 282. The open end of the socket 285 projects through an opening in the bottom of an open-topped socket box 291, made of specular material, which is mounted on two legs of the socket bracket 281 as shown in FIG. 16. The specular surface of the box 291 reflects light and heat from the part of a lamp 290 which is not surrounded by the reflector 250.

In the embodiment shown, the socket 285 is adapted to receive a tungsten halogen lamp 290, specifically a 75-watt Sylvania single-ended Q/CL 28 V., but the use of the particular lamp is not a part of this invention. In this embodiment, the voltages supplied to the lamp are approximately 22 and 27 for reading and examination respectively.

As shown in FIG. 16, the lamp 290 projects through the lamp opening 252 and into the reflector 250.

The lamp socket 285 has electrical lead ears 287 projecting from diametrically opposite sides. A conductor 288 electrically connected to the tab 262 of one of the lamp spring contacts 260 is electrically connected directly to one of the lead ears 287 of the socket 285. An electrical conductor 289 connected to the other lead ear 287 extends through an insulating bushing in the socket mounting plate 275 and a hole in the socket mounting plate insulator 276 to a rotary switch 300 mounted in a central opening in the outer wall of the hub 267. Another conductor 292 extends from the switch 300 to the other of the lamp spring contact lead connecting tabs.

Except for a mounting nut 299, an end of a switch barrel 298 on which the nut 299 is threaded, and the electrical conductors 289 and 292, the space within the cup-shaped hub 267 is filled with insulating material such as fiberglass 283.

It will be seen that the lamp 290, its socket 285, switch 300 and the electrical connections necessary to supply current from the spring contacts 213 are all self-contained upon the light head housing closure 265. The light head housing closure 265 is held positively in place by the socket head screws 259, which serve the double function of retaining the light head housing closure positively and of ensuring that the lamp spring contacts 260 are held tightly against the spring contacts 213.

When the socket head screws 259 are removed and the light head housing closure pulled straight away, as for relamping, the withdrawing of the lamp spring contacts 260 with the light head housing closure breaks all electrical contact with the source of current, so that the lamp can be replaced safely. At the same time, the position of the ends 215 of the contact springs 213 well inboard of the rear end of the light head housing, and between the inner wall of the housing and the radiation shield 230 ensures that no one is likely to receive a shock by touching one of the springs 213. As has been described heretofore, insulation 231 fills the space between the radiation shield 230 and the inner wall of the light head housing 201. In order to provide for sure electrical contact, without the interruption of insulation between the contact springs 213 and 260, longitudinal ribs can be provided on either side of the contacts, integral with and projecting inwardly from the side walls 204, and a closure strip.

Merely by way of illustration, the yoke 185, the light head housing 201 and the light head housing closure 265 can be moulded of polycarbonate plastic. The retard-stop disc 90 can be made of polypropylene. The boom members can be made of extruded aluminum.

In assembling the components of the system, the track and mounting system is first installed. An opening at the reference wall end, for which a removable cover is provided, permits the insertion within the carriage tracks of far end wheel blocks 49 which are initially unmounted to the carriage but are connected to the insulation block 174 on the free end of the flat tape conductor 170 as shown in FIG. 1. The carriage and near end wheel block, which is mounted on the carriage, are then mounted in the carriage tracks 30, and the far wheel block mounted, in place, on the ends of the throughbolts 48. The connector plugs 167 and 168 can then be plugged together.

The boom 5 has preferably been mounted within the boom mount 70, but the yoke assembly and reading-examination light are not attached. To install the yoke and light assembly, it is only necessary to remove the screws from the swivel boss insert 195, slide the swivel boss onto the end of the yoke swivel collar, and replace the swivel boss insert 195. The contact rings 182 and 160 mate, as do the contact plates 183 and 161. One of the contact rings and one of the contact plates may be made undulant, to ensure good contact.

It will be observed that in the system of this invention, all electrical contacts and connections are enclosed in such a way that the patients in the hospital beds and the nurses, doctors, attendants and maintenance people are protected against shock, and the opportunity for arcing or sparking is practically eliminated. It will be observed that the only sliding contacts are within the yoke fitting boss assembly, and within the yoke arms, at places entirely housed within electrically insulative material.

Figure 2:
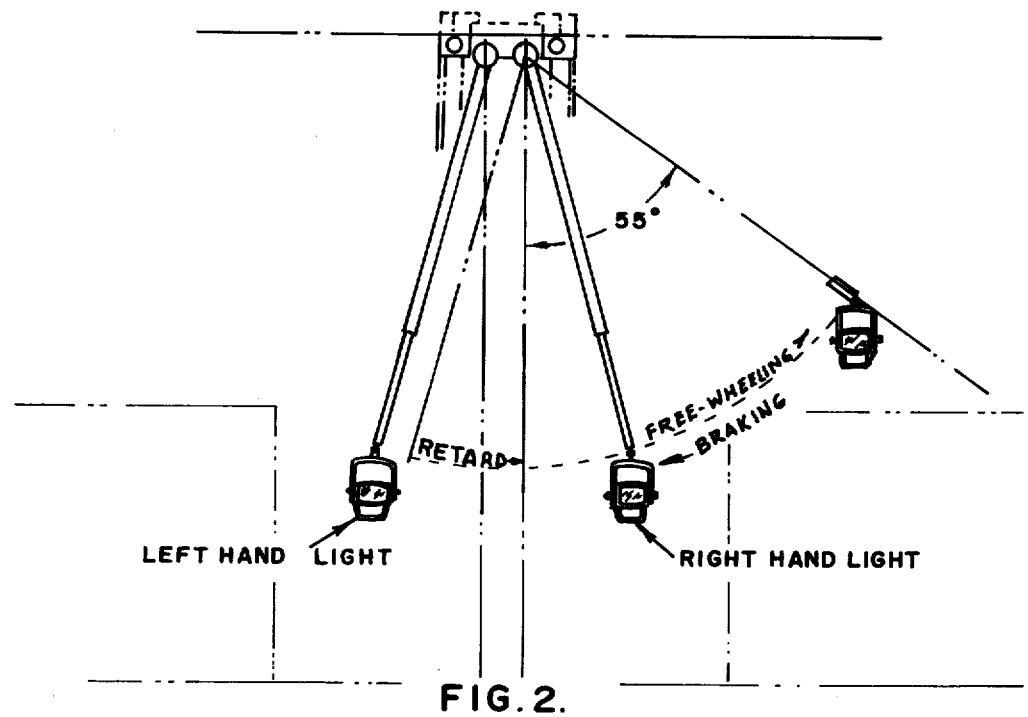
FIG. 2 is a somewhat diagrammatic view in end elevation illustrating the rotation of the lighting boom in one plane.

Numerous variations in the construction of elements of the system of this invention, within the scope of the appended claims, will be apparent to those skilled in the art in the light of the foregoing disclosure. For example, a two-way clutch can be provided with a throw-out mechanism at the vertical position, the eliminate the need for the retard-brake mechanism. The function of the present system involving the retard-stop disc 90 and rollpins 100 and 101 is to prevent free swinging of the examination lights and booms from a position past the vertical in a direction away from a hospital bed with a one-way clutch. It can be seen by referring to FIG. 2 that if the righthand light, for example, is pulled to the position shown by a broken line to the left of the vertical, the one-way clutch mechanism will offer no resistance to the swinging of the light boom to and past the vertical. The configuration of the grooves is such as to engage the rollpins through the travel of the boom through 35° to the "far" side of vertical, so that the light stays where it is put until it is returned to the vertical. The grooves and rollpins also serves as swing-limiting stops, permitting a swing of 55° in the direction of the beds and 35° away from the beds, from the vertical. A two-way clutch could be used for the same purpose, but it will be seen that a throw-out mechanism would be necessary to permit free-wheeling movement of the light in a direction toward the bed from the vertical.

In the embodiment shown, a three-position switch, mounted on a console on the reference wall, and provided with an indicator light which is turned on when the switch is at the high position, controls the voltage delivered to the lamp 290, the switch 300 serving as an on-off switch for the convenience of the patients. If the ribbon conductor were made with three conductive strips or if suitable internal circuitry were provided to regulate the voltage, the switch 300 could be made a three-position switch, in one of which the current supplied to the lamp produces sufficient illumination for reading, not for examination, while another position provides sufficient current for high-intensity illumination for examination purposes.

In the preferred embodiment shown, the yoke assembly and light are self-leveling in one plane by virtue of the spacer function of the pintle bosses 148, the ends of which abut and which keep sufficient clearance between the radial surfaces outboard of the circles 147 and the flat outside radial surfaces of the ring 143 to ensure easy movement of the yoke hinge 145. This, too, can be modified by using a ball-type mounting or a fixed type, but the preferred embodiment has distinct advantages, the swiveling of the yoke on the yoke fitting 140 and the pivoting of the light on the yoke providing a universal adjustment from the reference level.

The fore and aft braked swinging mounting of the boom on the carriage can also be modified or eliminated, but it, too, has desirable advantages in permitting easy manipulation by the examining physician without having to move the carriage for each new position and positioning of the reading-examination light beyond the travel of the carriage at both ends of the track, stops on the track limiting that travel to protect the flat tape conductor. A sliding contact can be used, but its use would be difficult because of the rigid requirements of shielding against exposed arcing.

The provision of the diffusing insert in the fluorescent fixture of fixtures produces unique and highly desirable light distribution. With a conventional prism arrangement on the outboard side wall of the primary enclosure in which the inside, longitudinal prisms, sixteen per inch, are at 45° on the lower side and 25° on the upper side from a plane perpendicular to the plane of the side wall, and the transverse outside prisms, ten per inch, are equilateral, with an included angle of 105°, a plot of candlepower distribution in a plane transverse to the length of the fixture takes the form of an inverted butterfly, with a large lobe in the direction of the floor and wall beyond the bed, a somewhat smaller lobe in the direction of the ceiling and a much reduced area directly over the bed, by virtue of the diffuser. In the longitudinal plane, the plot is substantially circular, as would be expected from a planar translucent fixture, but the intensity is much reduced on account of the low transmisivity of the diffusing insert. This provides a bright wall wash as well as illumination of the ceiling, which makes the entire room attractive and well illuminated but at the same time a patient sees only a comfortable level of illumination whether lying down or sitting up. This permits the use of a ceiling mounted or recessed television set, for example. Other arrangements can be used, such for example as a primary enclosure with a linear bat-wing prism pattern on its lower wall, but no other arrangment has been found to give as desirable a lighting pattern as that of the preferred embodiment described.

Having thus described the invention, what is claimed and desired to be secured by Letters Patent is:

1. In an illumination system for a medical facility, wherein a carriage track is mounted overhead and a carriage is mounted for movement along said carriage track, said carriage track extending from near a reference wall to a point distant from said reference wall, the improvement comprising said carriage track having spaced parallel ledges, said carriage having a plurality of wheels revolvably mounted on said carriage and resting upon said ledges, and a boom mount supported by said carriage and depending below said track; a boom swingably mounted in said boom mount; a lamp supported by said boom; electrical conductors carried by said boom and extending into said boom mount; a multiconductor-strip ribbon conductor disposed in a channel defined in part by one ledge of said track, said ribbon conductor being oriented with broad surfaces perpendicular to said ledge, and being of a length greater than the lengthwise travel of said carriage, said ribbon conductor being flexible and being doubled back intermediate its ends, said ribbon conductor being electrically connected at one of its ends to a source of current and at its other end to said electrical conductors carried by said boom.

2. In an illumination system for a medical facility, wherein a carriage track is mounted overhead and a carriage is mounted for movement along said carriage track, said carriage track extending from near a reference wall to a point distant from said reference wall, the improvement comprising said carriage having a plurality of wheels revolvably mounted on said carriage and resting upon said track; a boom mount supported by said carriage and depending below said track, a boom mounted on said boom mount, and a lamp supported by said boom; said boom mount being mounted for rotation on an axis parallel to the direction of travel of said carriage, and means for mounting said boom in said boom mount for rotation about an axis substantially perpendicular to the direction of travel of said carriage; said means comprising a first brake disc fixed against rotation with respect to said carriage, a first clutch washer mounted against rotation with respect to said boom mount and engaging a flat face of said first brake disc; and a second brake disc fixed against rotation with respect to said boom mount, a second clutch washer fixed against rotation with respect to said boom and engaging a flat face of said second brake disc; and means for biasing said brake discs and said clutch washers continuously into engagement.

3. In an illumination system for a medical facility, wherein a carriage track is mounted overhead and a carriage is mounted for movement along said carriage track, said carriage track extending from near a reference wall to a point distant from said reference wall, the improvement comprising said carriage having a plurality of wheels revolvably mounted on said carriage and resting upon said track, and a boom mount carried by said carriage and depending below said track, said boom mount being mounted for rotation on an axis parallel to the direction of travel of said carriage; a boom swingably mounted in said boom mount; a lamp supported by said boom; a clutch mechanism carried by said carriage for permitting said boom to rotate freely in one direction in a plane at right angles to the direction of travel of said carriage; and yieldable brake means carried by said carriage for permitting said clutch and boom to be rotated against the resistance of said brake means when said boom is rotated in the opposite direction in said plane.

4. In an illumination system for a medical facility, wherein an elongated boom is mounted to depend from above a patient and a reading-examination light is mounted on the lower end of said boom, the improvement comprising said boom being hollow and having at its lower end a yoke fitting including a yoke hinge, said yoke hinge being self-leveling in one plane, a swivel bearing section, an electrically insulative disc seated in said swivel bearing section and carrying on its outer face an outer contact ring and a center contact face, and electrical conductors carried by said boom and elecrically connected to said contact ring and contact plate.

5. In an illumination system for a room of a medical facility, wherein a patient is oriented along an axis substantially perpendicular to a reference wall, the improvement comprising an elongated carriage track and an elongated fluorescent lighting fixture, said carriage track and said lighting fixture extending from a point near said reference wall to a point distant from said reference wall along an axis substantially perpendicular to said wall and generally above said patient position, said carriage track and said lighting fixture being parallel and in spaced relation to one another; an elongated primary lamp enclosure for said lighting fixture, said primary enclosure depending below the plane of said carriage track, said primary enclosure having transparent, high transmitting bottom and side walls, and separate means for reducing light transmission and brightness of said bottom wall and a first side wall of said primary enclosure, said first side wall facing said carriage track; a carriage mounted for movement along said carriage track, a boom mount supported by said carriage and depending below said track, an elongated boom supported by said boom mount, said boom having a first section and a second section, said second section slidably engaging said first section; and a yoke mounted reading-examination light on the end of said boom; said reading-examination light being rotatably mounted in said yoke, said yoke being self-leveling and revolvably mounted to said boom, said boom being extendable and swingably mounted in said boom mount for positioning fore and aft about an axis substantially perpendicular to the direction of travel of said carriage, said boom mount being rotatably mounted in said carriage permitting said boom to rotate in a plane perpendicular to the direction of travel of said carriage; means for holding said boom in any elevated position inscribed within a cone having its vertex on the center axes of said boom mount; and means for the solid electrical connection of a lamp in said reading-examination light to a source of current near one end of said carriage track.

6. The improvement of claim 5 wherein two of said fluorescent lighting fixtures are positioned one on each side of and in spaced relation to said carriage track.

7. The improvement of claim 5 wherein two said carriage tracks are positioned one on each side of an elongated central curtain track, said carriage tracks and said lighting fixtures being paired and in spaced relation to said curtain track.

8. The improvement of claim 4 including a yoke, swivelably mounted on said swivel bearing section, said yoke having a swivel boss having a seat in which a disc of electrically insulative material is mounted, said disc carrying on its outer face a contact ring and center contact corresponding to and correlating with the contact ring and center contact of the boom yoke fitting, said yoke having a hollow cross piece and hollow arms, each of said arms carrying an electrical conductor connected to one of said contact ring and center contact, each of said arms having a transverse passage therethrough, a contact spring within said arms electrically connected to said conductor, and constructed to engage an electrically conductive sleeve extending into said passage.

9. In an illumination system for hospital rooms, wherein a central curtain track is flanked by lighting boom carriage tracks, said carriage tracks are mounted overhead and a carriage is mounted for movement on each said carriage track, said carriage tracks extending from near a reference wall to a point beyond the end of a bed extending from said reference wall, the improvement comprising each of said carriages having a plurality of wheels revolvably mounted on said carriage and resting upon said track and a boom mount supported by said carriage, mounted for rotation on an axis parallel to the direction of travel of said carriage and depending below said track; a boom swingably mounted in said boom mount; a lamp supported by said boom; and a clutch and retard mechanism mounted between said boom mount and said carriage, said clutch and retard mechanism comprising a one way clutch mechanism for permitting said boom to swing freely in a direction away from the said curtain track and to lock against movement toward said curtain track; yieldable brake means rotatably carried by said carriage for permitting clutch and boom to be rotated against the resistance of said brake means in a direction toward the curtain track and past the vertical, and retard means for retarding the rotation of said boom to and from the vertical from a position beyond the vertical in the direction of said curtain track.

10. The improvement of claim 9 wherein the retard means comprises a retard disc with arcuate passages, narrower through a part of their arcuate length than through another part of their arcuate length, said retard disc being fixed against rotation with respect to the carriage, and a plate adjacent said retard disc, fixed to rotate with said boom mount and having roll pins fixed in said plate at one end and projecting into said retard disc passages at their other end.

11. In a yoke-mounted hospital reading-examination light wherein spaced arms of a yoke carry electrical conductors to a yoke contact the improvement comprising contact sleeves of electrically conductive material mounted in side walls of a light housing, projecting outboardly thereof and inboardly thereof, journaled for rotation in said yoke arms, each of said sleeves being in rotatable physical and electrical contact with said yoke contact in one arm and in fixed physical and electrical contact with a housing spring contact inside said light housing, each of said spring contacts extending along an inside surface of said side walls toward a rear opening in said housing, a light housing closure, said closure carrying spring contacts complementary to and engaging physically and electrically the housing spring contacts when the closure is mounted on the rear of the housing and disengaging when the said closure is removed, and a switch, mounted on said closure and electrically connected to said spring contacts.

* * * * *